(12) United States Patent
Palazzotto et al.

(10) Patent No.: US 9,702,840 B2
(45) Date of Patent: Jul. 11, 2017

(54) PORTABLE ELECTRONIC DEVICE AND VAPOR SENSOR CARD

(71) Applicant: 3M INNOVATIVE PROPERTIES COMPANY, St. Paul, MN (US)

(72) Inventors: Michael C. Palazzotto, Woodbury, MN (US); Stefan H. Gryska, Woodbury, MN (US); Justin Tungjunyatham, Roseville, MN (US); Ryan D. Erickson, Roseville, MN (US); Jaime B. Willoughby, Hugo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 217 days.

(21) Appl. No.: 14/415,079

(22) PCT Filed: Jul. 23, 2013

(86) PCT No.: PCT/US2013/051665
§ 371 (c)(1),
(2) Date: Jan. 15, 2015

(87) PCT Pub. No.: WO2014/022155
PCT Pub. Date: Feb. 6, 2014

(65) Prior Publication Data
US 2015/0185175 A1 Jul. 2, 2015

Related U.S. Application Data

(60) Provisional application No. 61/678,806, filed on Aug. 2, 2012.

(51) Int. Cl.
*G01N 27/22* (2006.01)
*G01N 33/00* (2006.01)

(52) U.S. Cl.
CPC ........... *G01N 27/22* (2013.01); *G01N 27/223* (2013.01); *G01N 27/226* (2013.01);
(Continued)

(58) Field of Classification Search
None
See application file for complete search history.

(56) References Cited

U.S. PATENT DOCUMENTS

| 6,085,576 A | 7/2000 | Sunshine |
| 7,348,088 B2 | 3/2008 | Hamrock |

(Continued)

FOREIGN PATENT DOCUMENTS

| EP | 2352024 | 3/2011 |
| FR | 2687834 | 8/1993 |

(Continued)

OTHER PUBLICATIONS

Budd, "Free volume and intrinsic microporosity in polymers", Journal of Materials Chemistry, Jan. 2005, vol. 15, pp. 1977-1986.
(Continued)

*Primary Examiner* — Melissa Koval
*Assistant Examiner* — Felicia Farrow
(74) *Attorney, Agent, or Firm* — Bradford B. Wright; Yufeng Dong

(57) ABSTRACT

A portable device includes an outer housing including an inlet port and a outer slot adapted to receive a vapor sensor card; an operating circuit disposed at least partially within the outer housing; a sensor holder at least partially disposed within the outer housing. The sensor holder includes: an inner housing including a gas intake chamber in downstream fluid communication with the inlet port. The gas intake chamber has a gas outlet in fluid communication with an inner slot retaining a sensor card socket for engaging the vapor sensor card. The sensor holder further comprises an
(Continued)

electrical heater element, a fan, and a turbulent-flow-inducing member. The vapor sensor card comprises a sensor housing and a capacitive sensor element.

12 Claims, 9 Drawing Sheets

(52) U.S. Cl.
CPC ..... *G01N 33/0004* (2013.01); *G01N 33/0009* (2013.01); *G01N 2027/222* (2013.01)

(56) References Cited

U.S. PATENT DOCUMENTS

| | | | |
|---|---|---|---|
| 2004/0069046 | A1* | 4/2004 | Sunshine ........... G01N 33/0031 73/23.34 |
| 2006/0246273 | A1 | 11/2006 | McKeown |
| 2011/0031983 | A1 | 2/2011 | David |
| 2011/0045601 | A1 | 2/2011 | Gryska |
| 2011/0254568 | A1 | 10/2011 | Thomas |
| 2014/0028333 | A1* | 1/2014 | Palazzotto ........... G01N 27/123 324/658 |

FOREIGN PATENT DOCUMENTS

| | | |
|---|---|---|
| WO | WO 2004-048959 | 6/2004 |
| WO | WO 2005-012397 | 2/2005 |
| WO | WO 2009-045733 | 4/2009 |
| WO | WO 2009-046011 | 4/2009 |
| WO | WO 2010-075333 | 7/2010 |
| WO | WO 2011-159480 | 12/2011 |
| WO | WO 2012-044419 | 4/2012 |
| WO | WO 2012-050686 | 4/2012 |
| WO | WO 2012-141883 | 10/2012 |
| WO | WO 2012-141894 | 10/2012 |
| WO | WO 2012-141925 | 10/2012 |
| WO | WO 2012-141958 | 10/2012 |
| WO | WO 2012-170248 | 12/2012 |
| WO | WO 2013-049035 | 4/2013 |
| WO | WO 2013-090188 | 6/2013 |
| WO | WO 2013-090191 | 6/2013 |
| WO | WO 2013-180936 | 12/2013 |
| WO | WO 2014-003979 | 1/2014 |
| WO | WO 2014-075246 | 5/2014 |

OTHER PUBLICATIONS

Budd, "Polymers of intrinsic microporosity (PIMs): robust, solution-processable, organic microporous materials", Chemical Communications, 2004, vol. 2, pp. 230-231.

Carta, "Novel Spirobisindanes for Use as Precursors to Polymers of Intrinsic Microporosity", Organic Letters, 2008, vol. 10, No. 13, pp. 2641-2643.

Ghanem, "High-Performance Membranes from Polyimides with Intrinsic Microporosity", Advanced Materials, 2008, vol. 20, pp. 2766-2771.

Ghanem, "Polymers of Intrinsic Microporosity Derived from Bis(phenazyl) Monomers", Macromolecules, 2008, vol. 41, No. 5, pp. 1640-1646.

McKeown, "Polymers of Intrinsic Microporosity", Chemistry, A European Journal, 2005, vol. 11, pp. 2610-2620.

International Search Report for PCT International Application No. PCT/US2013/051665, mailed on Dec. 17, 2013, 5 pages.

* cited by examiner

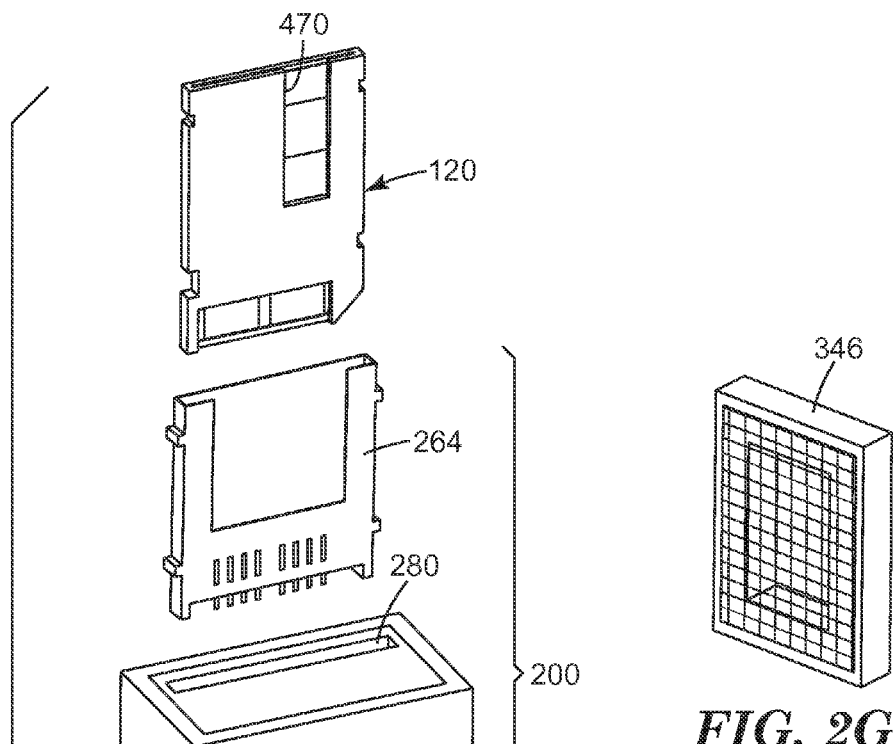
*FIG. 2E*
*FIG. 2G*
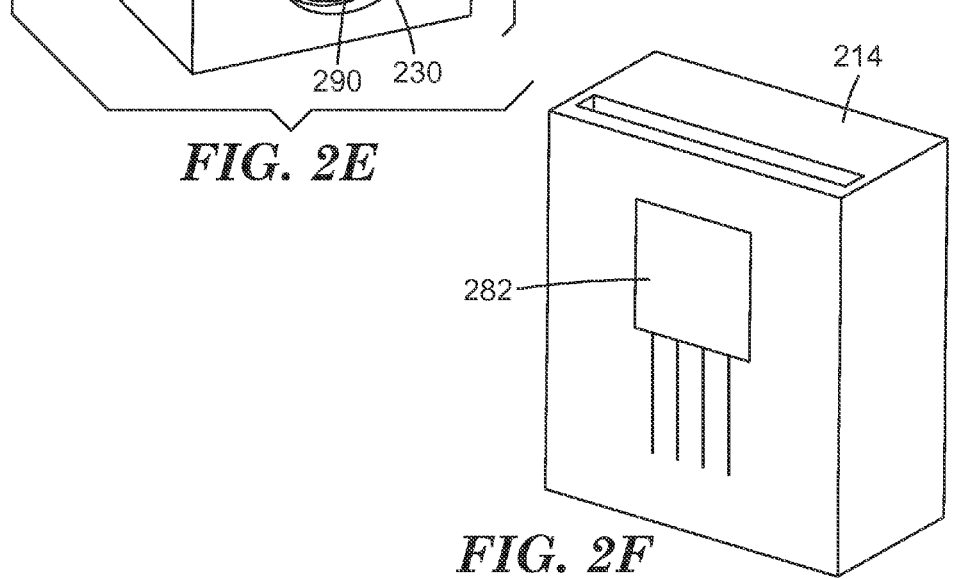
*FIG. 2F*

PORTABLE ELECTRONIC DEVICE AND VAPOR SENSOR CARD

TECHNICAL FIELD

The present disclosure relates broadly to electronic sensors for detecting vapors.

BACKGROUND

The detection of volatile organic compounds (VOCs) and humidity has many commercial, public, and residential applications due to environmental and safety concerns. One useful sensor type is a capacitive sensor in which a sorbent material is disposed between two electrodes. Typically, at least one of the electrodes is porous or otherwise permeable by the analyte vapor to be measured. Examples of sorbent materials used in these types of sensors include so-called Polymers of Intrinsic Microporosity (PIMs, for VOC measurement) and sulfonated fluoropolymers (for humidity measurement).

Most commercially available organic vapor sensor systems are based on the Photo-Ionization Detector (PID) technology. Even though PID sensing technology is common, it has its limitations, such as large size, high cost, and high power consumption. For applications wherein ambient air quality is of concern (e.g., in a factory or other workplace), portability is highly desirable. Ease of operation, ease of maintenance, and cost are also important concerns. There is a continuing need for new organic vapor sensor systems that provide improvement relative to at least one of the above-mentioned problems.

SUMMARY

In one aspect, the present disclosure provides a portable device comprising:
an outer housing including an inlet port and a outer slot adapted to receive a vapor sensor card;
an operating circuit disposed at least partially within the outer housing;
a sensor holder at least partially disposed within the outer housing, wherein the sensor holder comprises:
an inner housing including:
a gas intake chamber in downstream fluid communication with the inlet port, wherein the gas intake chamber has a gas inlet and a gas outlet;
a inner slot retaining a sensor card socket adapted to engage the vapor sensor card, wherein the inner slot is in fluid communication with the gas inlet through the gas intake chamber;
an electrical heater element in electrical communication with the operating circuit and in thermal communication with the sensor card socket;
a fan disposed such that it a directs gas from the inlet port to the gas outlet; and
a turbulent-flow-inducing member adjacent to and extending across at least a portion of the gas outlet.

In some embodiments, the sensor card socket engages a vapor sensor card comprising a capacitive sensor element in electrical and thermal communication with the sensor card socket.

Accordingly, in another aspect, the present disclosure provides a vapor sensor card comprising:
a sensor housing having first and second opposed major surfaces, wherein the capacitive sensor element has a longitudinal channel abutting the first major surface, wherein the longitudinal channel has a bottom surface; and
a capacitive sensor element forming at least a portion of the bottom surface, wherein the capacitive sensor element comprises:
a conductive base electrode disposed on a support member;
a conductive porous electrode, wherein the conductive porous electrode comprises a portion of a bottom surface of the longitudinal channel, and wherein the conductive porous electrode comprises at least a portion of an outer surface of the vapor sensor card; and
a dielectric detection layer comprising a sorbent material disposed between the conductive base electrode and the conductive porous electrode; and
a first conductive pathway in electrical communication with the conductive base electrode and extending outside the sensor housing; and
a second conductive pathway in electrical communication with the conductive base electrode and extending outside the sensor housing.

Portable devices and vapor sensors according to the present disclosure can be fabricated relatively inexpensively (e.g., as compared to existing photoionization detectors available in the marketplace), and compactly. Portable vapor sensors according to the present disclosure are typically reliable and easy to use, and have a externally accessible replaceable sensor element should replacement become necessary for any reason. Advantageuously, portable vapor sensors according to the present disclosure have advantages over existing detection PID vapor detection technology in their relatively low cost, reproducibility, and accuracy in detecting organic vapors. Another advantage to this design is the incorporation of the disposable sensor concept. This concept allows user to easily replace the sensor inside the device.

As used herein:
the term "conductive" means electrically conductive unless otherwise specified;
the term "in downstream fluid communication" means in the direction of gas flowing from the inlet to the outlet channel through the device; and
the unmodified term "fan" refers to any device for creating a current of gas (e.g., air) by movement of a surface or number of surfaces.

Features and advantages of the present disclosure will be further understood upon consideration of the detailed description as well as the appended claims.

BRIEF DESCRIPTION OF THE DRAWINGS

FIG. 2E is an exploded perspective view of sensor holder 200 with vapor sensor card 120 inserted therein.

FIG. 2F is a front perspective view of second inner member 214 with electrical heater element 282 engaged therewith.

FIG. 2G is an enlarged perspective view of turbulent-flow-inducing member 346.

Figures 1A, 1B:
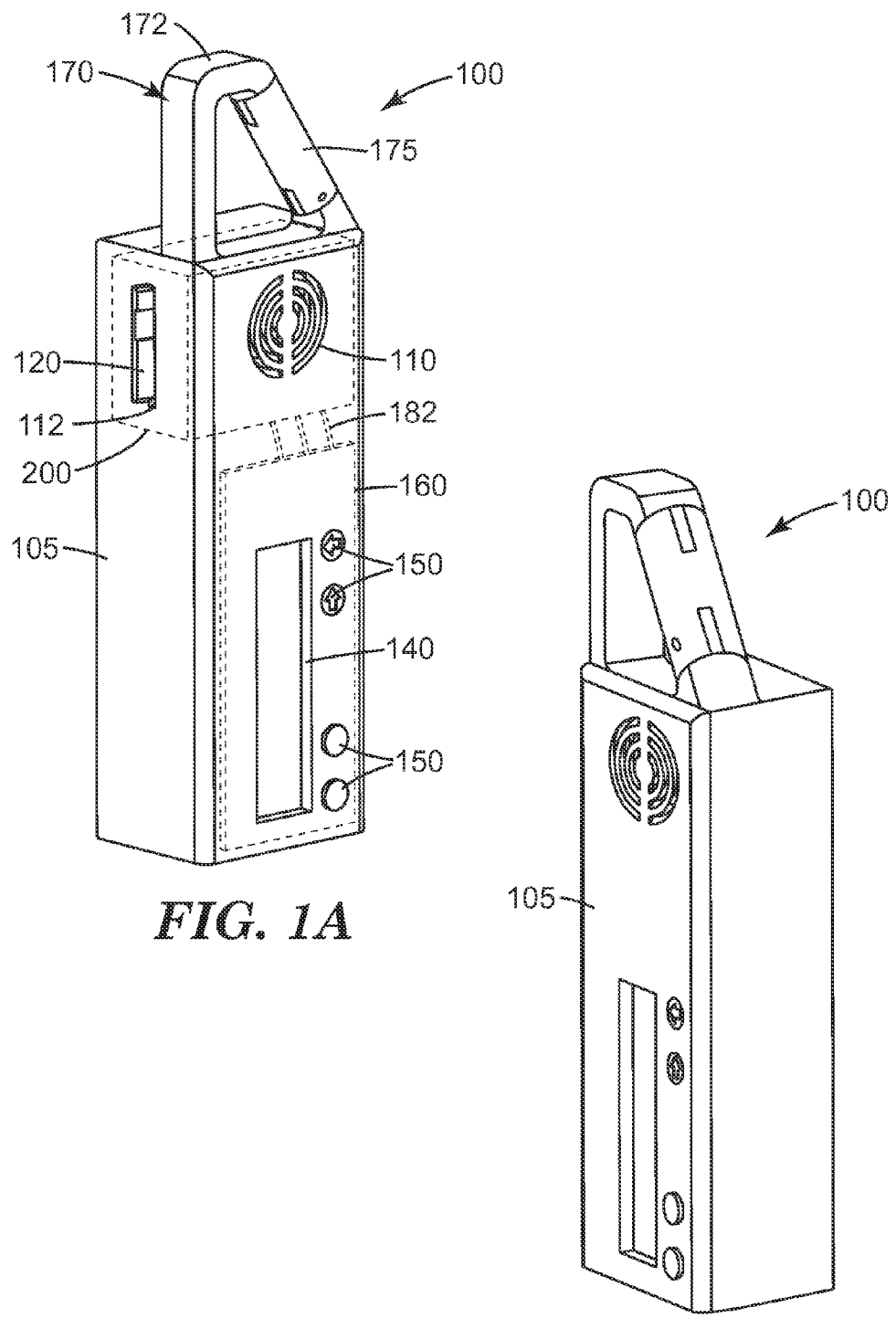
FIG. 1A is a perspective view of portable device 100 according to one embodiment of the present disclosure.
FIG. 1B is a reverse perspective view of portable device 100.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figures may not be drawn to scale.

DETAILED DESCRIPTION

In one exemplary embodiment, shown in FIGS. 1A and 1B, portable device 100 comprises outer housing 105. Outer housing 105 includes inlet port 110 and outer slot 112 adapted to receive vapor sensor card 120. Attachment member 170, which includes handle 172 and spring clip 175, is affixed to outer housing 105, and provides convenient attachment to clothing and/or accessories worn by a user or to a fastener (e.g., a screw eye) situated at a specific location of interest. Outer housing 105 may comprise, for example, one integral part or multiple parts that engage (e.g., mechanically and/or adhesively). Sensor holder 200 is disposed within outer housing 105 and in electrical communication with operating circuit 160 through conductive members 182. Electronic display 140 is communicatively coupled to operating circuit 160 disposed within outer housing 105. Manually operable controls 150 allow a user to control the operating circuit and the electronic display.

While the outer housing may have openings for an electronic display and operator controls, it will be recognized that these components may alternatively or in addition be contained within the housing. For example, the housing may be made of a transparent material (e.g., a clear plastic) that permits readability of the electronic display, which is contained within the housing. Likewise, the operator controls may be accessible through the housing; for example, as in the case of inductive proximity sensor controls.

Figure 2A:
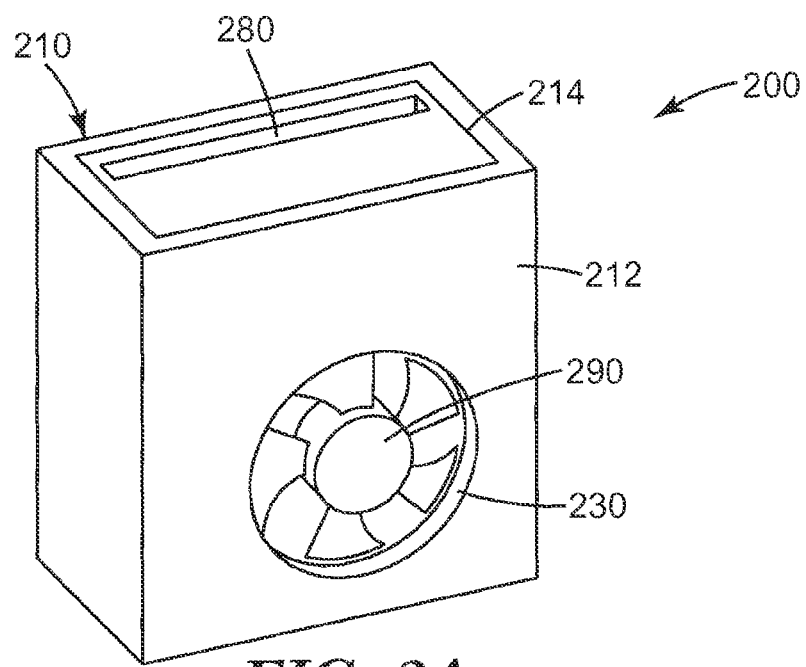
FIG. 2A is a perspective view of sensor holder 200.
Figure 2B:
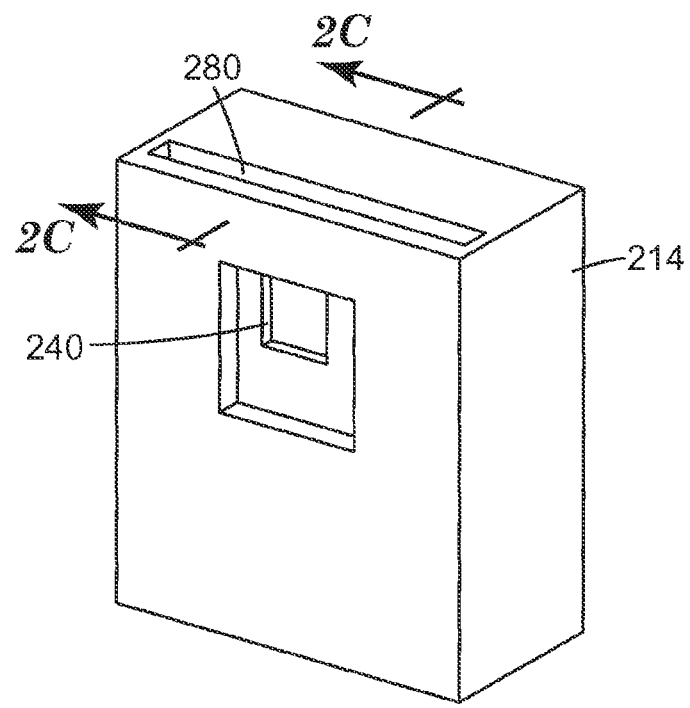
FIG. 2B is a front perspective views of second inner member 214.

Referring now to FIG. 2A sensor holder 200 comprises inner housing 210 with gas inlet 230 and fan 290. Inner housing 210 comprises first and second inner housing members 212, 214. First inner housing member 212 includes gas inlet 230. As shown in FIG. 2E, inner slot 280 retains sensor card socket 264 which engages vapor sensor card 120.

Figure 2C:
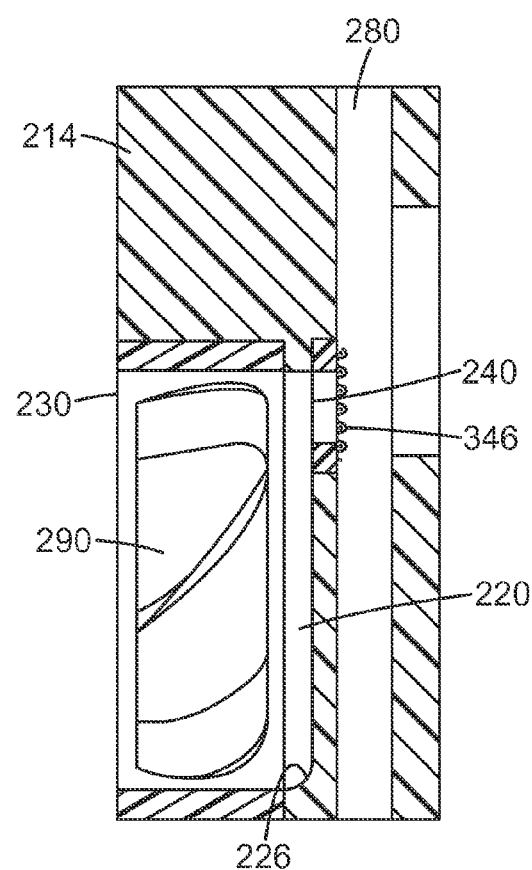
FIG. 2C is a cross-sectional view of FIG. 2B.
Figure 2D:
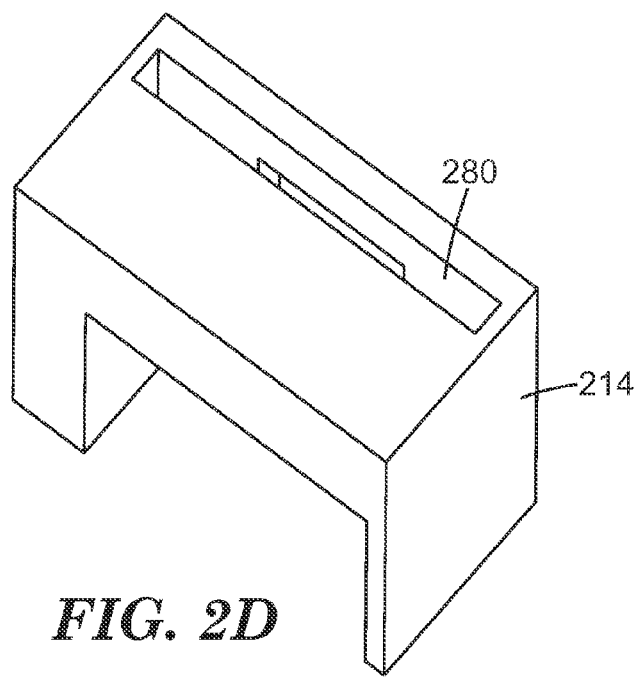
FIG. 2D is a back perspective views of second inner member 214.

Referring now to FIGS. 2C and 2D, inner slot 280 is adjacent and in downstream fluid communication with gas outlet 240. Turbulent-flow-inducing member 346 (shown enlarged in FIG. 2G) is adjacent to and extends across gas outlet 240.

Referring now to FIG. 2F, electrical heater element 282 contacts sensor card socket 264 (not shown, see FIG. 2E) which is disposed in inner slot 280. Electrical heater element 282 is in electrical communication with operating circuit 160, and in thermal communication with sensor card socket 264.

As shown in FIG. 2C, fan 290, disposed within gas inlet 230, directs gas into gas intake chamber 220 and out of gas outlet 240.

The outer and inner housings may be made of any suitable material capable of withstanding the intended use. Examples include metal, thermosets (e.g., Bakelite) and thermoplastics (e.g., engineering plastics such as polyimides, polyether ketones, polyether ether ketones, and polyphenylene sulfides).

The turbulent-flow-inducing member serves to cause turbulence in the gas stream (e.g., through vortex shedding) as it leaves the gas outlet. The turbulent-flow-inducing member may be constructed of plastic, metal, glass, or any other material that is dimensionally stable and does not outgas appreciably. The present inventors have determined that turbulent gas flow across the conductive porous electrode can reduce response time of the capacitive sensor element. Any porous structure may be used as the turbulent-flow-inducing member. In some embodiments, the turbulent-flow-inducing member comprises a mesh (for example, a wire mesh such as, e.g., a 34-gauge steel wire mesh, model 30×30, from Peace Wire Mesh Works, Hengshui, Hebei, China)), fabric, or monolithic openwork (e.g., of molded plastic). As used herein, the term "openwork" refers to an ornamental or structural work containing numerous openings. In some embodiments, the openings are arranged in a regular array, although this is not a requirement.

Referring now to FIG. 2C, second inner housing member 214 and fan 290 form gas intake chamber 220. Gas intake chamber 220 is in downstream fluid communication from inlet port 110 (see FIG. 1A). Gas intake chamber 220 is downsteam from gas inlet 230 and upstream from gas outlet 240. In the embodiment shown, inner surfaces 226 of gas intake chamber 220 that are impinged upon by the gas are rounded at intersections of adjacent walls to mitigate the problem of uneven flow (e.g., "dead" spots). While it may be convenient for a manufacturing standpoint to assemble inner housing 210 from multiple component members, it is also possible to fabricate it as a unitary piece (e.g., by molding or rapid prototyping).

Figures 3A, 3B:
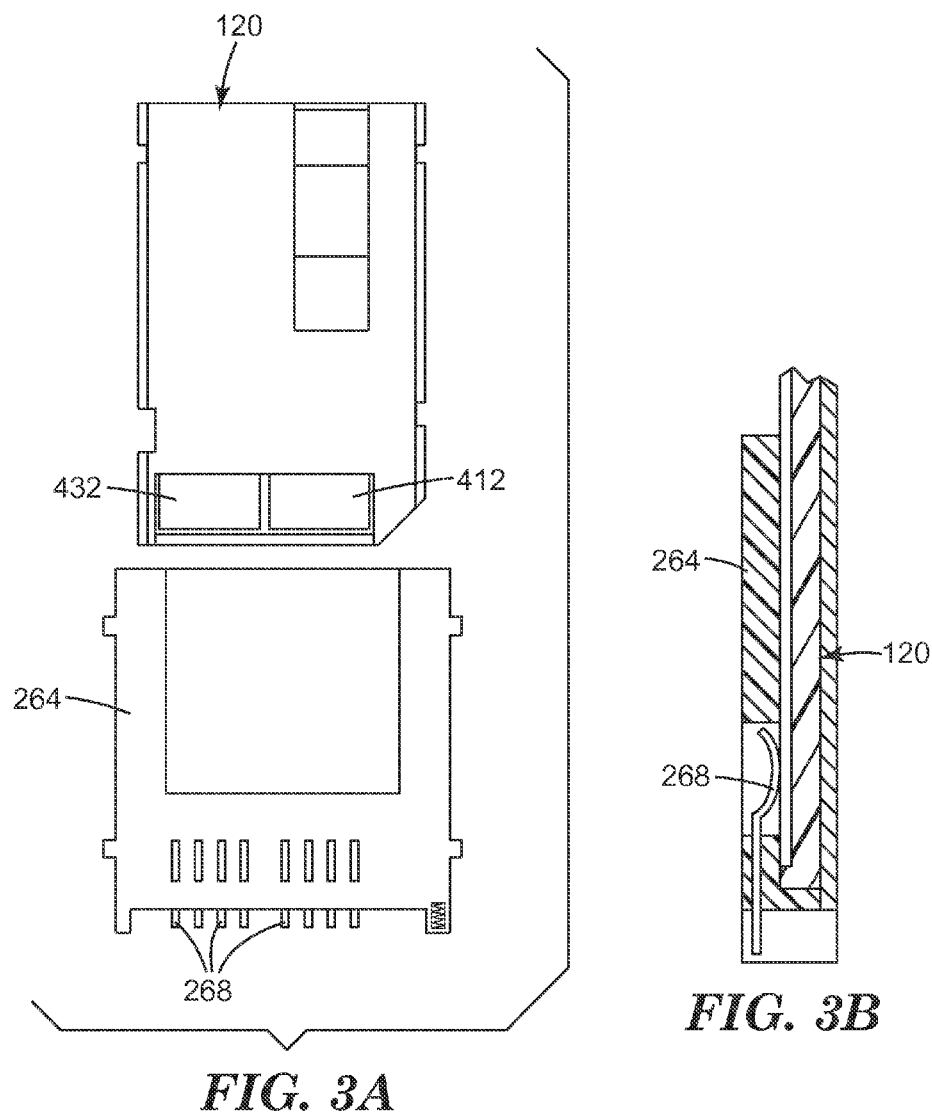
FIG. 3A is an exploded perspective view of exemplary vapor sensor card 120 inserted in sensor card socket 264.
FIG. 3B is a cross-sectional side view of vapor sensor card 120 inserted in sensor card socket 264.

Referring now to FIGS. 3A and 3B, when engaged with sensor card socket 264, vapor sensor card 120 forms electrical contact (i.e., electrical communication) between first and second conductive pathways 412, 432 (e.g., wires, traces, and/or tracks) and electrical terminals 268 of sensor card socket 264, which in turn are in electrical communication with operating circuit 160. Conductive pathways 412, 432 are in electrical communication with base conductive electrode and the porous conductive electrode, respectively. In some embodiments, sensor card socket 264 comprises an SD memory socket. In some embodiments, vapor sensor card 120 and/or sensor card socket 264 conforms to the Personal Computer Memory Card International Association PCMCIA 2.0 standard as to its form and electrical interconnections. In one embodiment, vapor sensor card 120 has the shape and size of an SD memory card.

Figure 4:
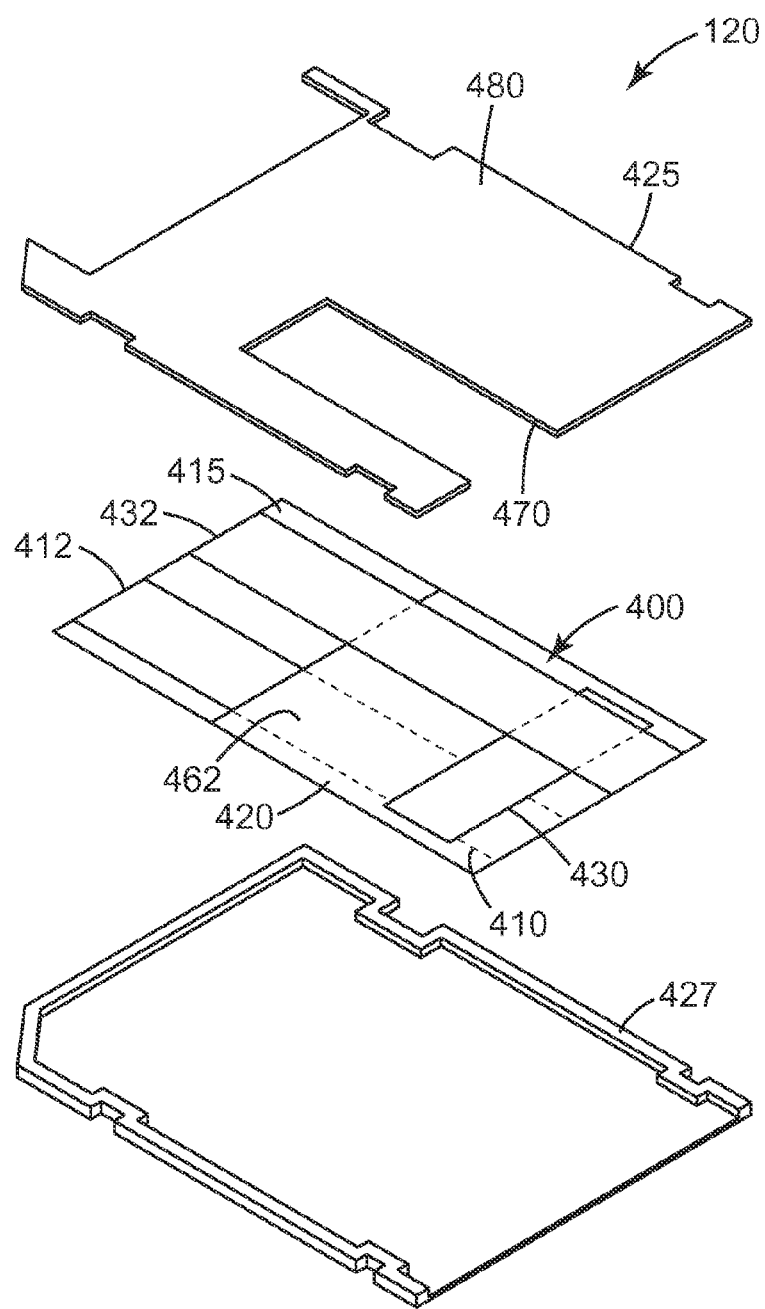
FIG. 4 is an exploded perspective view of sensor card 120.

Referring now to FIG. 4, exemplary vapor sensor card 120 comprises capacitive sensor element 400 disposed between upper and lower housing members 425, 427. Longitudinal channel 470 has bottom surface 462, and abuts major surface 480 of vapor sensor card 120. Capacitive sensor element 400 is disposed such that it forms a portion of bottom surface 462. As vapor sensor card 120 engages sensor card socket 264, longitudinal channel 470, extends through outer slot 112 in outer housing 105, thereby providing an outlet for gas (e.g., an ambient atmospheric sample) drawn through inlet port 110 into the portable device 100. While in the embodiment shown, gas exits the sensor device via the longitudinal channel, other configurations may also be used as long as at least one opening exists in the outer housing to permit exit of the gas. For example, the vapor sensor card may have no longitudinal channel, but a hole adjacent to the outer slot provides an avenue for gas to escape the outer housing.

Capacitive sensor element 400 comprises conductive base electrode 410 disposed on optional support member 415, conductive porous electrode 430, and dielectric detection layer 420, which comprises a sorbent material and is disposed between conductive base electrode 410 and conductive porous electrode 430. Capacitive sensor element 400 is retained in vapor sensor card 120 such the porous conductive electrode is disposed at the bottom of the longitudinal channel and contacts gas flowing through the longitudinal channel. In this configuration, capacitive sensor element 400 can be protected from accidental physical damage, and vapor sensor card 120 can be easily and/or safely handled.

When inserted into the sensor holder, conductive porous electrode 430 is in fluid contact with gas passing through the sensor holder. Conductive pathways 412, 432 extend from conductive base electrode 410 and conductive porous electrode 430, respectively. When vapor sensor card 120 is engaged with sensor card socket 264, conductive pathways 412, 432 come into electrical communication with electrical terminals 268.

Optional support member 415, which may be rigid or flexble, should have sufficient integrity to provide a degree of handleability to the sensor element. In some embodiments, the optional support member is substantially planar in shape so that it can be easily incorporated into the vapor sensor card. Examples of suitable optional support members include polymer films (e.g., polyester or polyimide), glass, paper, and cardboard. If the optional support member is not present, then the conductive base electrode will typically be mounted on an inner surface of one the vapor sensor card (e.g., in the case of a vapor sensor card assembled by engaging upper and lower portions).

The conductive base electrode and the conductive porous electrode may comprise any conductive material that is conductive. For example, the conductive base electrode may comprise a metal layer. Exemplary metals include noble metals (e.g., gold, platinum, iridium, palladium, osmium, silver, rhodium, and ruthenium). Combinations of different materials (conductive and/or nonconductive) can be used, as different layers or as a mixture, as long as sufficient overall conductivity is provided. Typically, the conductive base electrode and the conductive porous electrode have a sheet resistance of less than about $10^7$ ohms/square.

Examples of materials that can be used to make the conductive base electrode organic materials, inorganic materials, metals, alloys, and various mixtures and composites comprising any or all of these materials. In certain embodiments, coated (for example, thermal vapor coated, sputter coated, etc.) metals or metal oxides, or combinations thereof, may be used. Suitable conductive materials include for example aluminum, nickel, titanium, tin, indium-tin oxide, gold, silver, platinum, palladium, copper, chromium, and combinations thereof. The conductive base electrode can be of any thickness as long as it is conductive; for example, in a thickness in a range of from at least 4 nanometers (nm) to 400 nm, from at least 7 nm to 300 nm, or from at least 10 nm to 200 nm. For example, the conductive base electrode may have sufficient thickness to be self-supporting (e.g., in a range of from 10 micrometers to one centimeter), although greater and lesser thicknesses may also be used.

The conductive base electrode may comprise a conductive carbon fiber electrode. Such an electrode is described in U.S. Provisional Appln. No. 61/663,688, entitled "Sensor Element, Method of Making, and Method of Using the Same", filed Jun. 25, 2012 (Gryska et al.).

The conductive porous electrode may comprise any conductive material that is porous (including, e.g., microporous and nanoporous) to water vapor and/or at least one organic compound vapor. Examples of materials that can be used to make the conductive porous electrode include organic materials, inorganic materials, metals, alloys, and various mixtures and composites comprising any or all of these materials. In certain embodiments, coated (for example, thermal vapor coated, sputter coated, etc.) metals or metal oxides, or combinations thereof, may be used. Suitable materials for use in the conductive porous electrode include, for example, gold, silver, platinum, palladium, carbon nanotubes, and combinations thereof. Details concerning silver ink coated porous conductive electrodes can also be found in U.S. Patent Appl. Publ. 2011/0045601 A1 (Gryska et al.). Details concerning vapor-deposited vapor-permeable conductive electrodes can also be found in U.S. Provisional Patent Appln. No. 61/388,146 (Palazzotto et al.).

Combinations of different materials (conductive and/or nonconductive) can be used, as different layers or as a mixture, as long as sufficient overall conductivity and permeability is provided. The conductive porous electrode typically has a thickness in a range of from 1 nanometer (nm) to 500 nm, although other thicknesses may be used. For example, in embodiments in which the conductive porous electrode comprises vapor deposited gold, the conductive porous electrode may have a thickness in a range of from about 4 to about 9 nanometers (nm). In embodiments in which the conductive porous electrode comprises silver ink, the conductive porous electrode may have a thickness in a range of from about 50 to about 400 nm.

Greater thicknesses may have undesirably low levels of permeability, while lesser thicknesses may become insufficiently conductive and/or difficult to electrically connect to the second conductive member. Since the conductive porous electrode is permeable, the conductive base electrode typically comprises a continuous, uninterrupted layer, but it may contain openings or other interruptions if desired.

The sorbent material can be any dielectric material (e.g., inorganic or organic) that is microporous and is capable of absorbing at least one analyte vapor within its interior. In this context, the terms "microporous" and "microporosity" mean that the material has a significant amount of internal, interconnected pore volume, with the mean pore size (as characterized, for example, by sorption isotherm procedures) being less than about 100 nanometers (nm), typically less than about 10 nm. Such microporosity provides that molecules of vapor to be analyze (i.e., analyte) will be able to penetrate the internal pore volume of the material and take up residence in the internal pores. The presence of such analyte in the internal pores can alter the dielectric properties of the material such that a change in the dielectric constant (or any other suitable electrical property) can be observed.

The choice of the sorbent material will generally depend on the vapor to be analyzed. For example, if humidity (water vapor) is to be determined then a sorbent material comprising a hygroscopic material such as, for example, a sulfonated fluoropolymer may be advantageously used.

However, if it is desired to analyze for one or more volatile organic compounds, then a sorbent material comprising a so-called polymer of intrinsic microporosity (PIM) may be useful. PIMs are polymeric materials with nanometer-scale pores due to inefficient packing of the polymer chains. For example, in Chemical Communications, 2004, (2), pp. 230-231, Budd et al. report a series of intrinsically microporous materials containing dibenzodioxane linkages between rigid and/or contorted monomeric building blocks (i.e., monomeric units). Representative members of this family of polymers include those generated by condensation of Component A (e.g., A1, A2, or A3) with Component B (e.g., B1, B2, or B3) as shown in Table 1 according to Scheme 1.

SCHEME 1

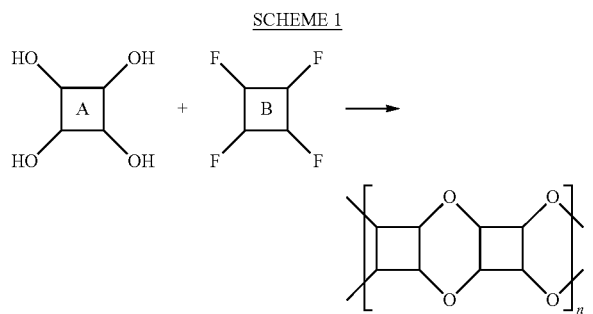

TABLE 1

COMPONENT A

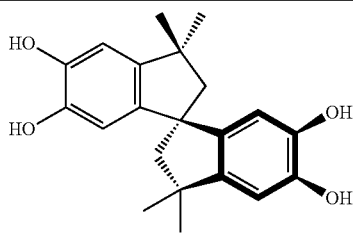

A1

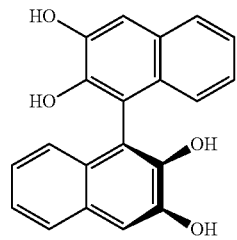

A2

TABLE 1-continued

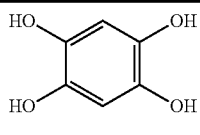

A3

COMPONENT B

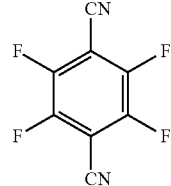 [SMILES: N#Cc1c(F)c(F)c(C#N)c(F)c1F]

B1

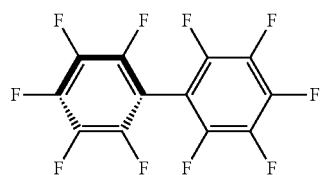

B2

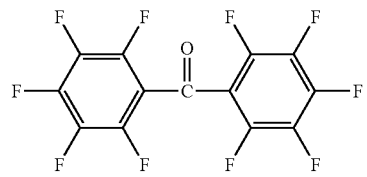 [SMILES: O=C(c1c(F)c(F)c(F)c(F)c1F)c1c(F)c(F)c(F)c(F)c1F]

B3

Further suitable Components A and B, and resultant intrinsically microporous polymers, are known in the art, for example, as reported by Budd et al. in *Journal of Materials Chemistry*, 2005, Vol. 15, pp. 1977-1986; by McKeown et al. in *Chemistry, A European Journal*, 2005, Vol. 11, pp. 2610-2620; by Ghanem et al. in *Macromolecules*, 2008, vol. 41, pp. 1640-1646; by Ghanem et al. in *Advanced Materials*, 2008, vol. 20, pp. 2766-2771; by Carta et al. in *Organic Letters*, 2008, vol. 10(13), pp. 2641-2643; in PCT Published Application WO 2005/012397 A2 (McKeown et al.); and in U.S. Patent Appl. Publ. No. 2006/0246273 (McKeown et al.).

Such polymers can be synthesized, for example, by a step-growth polymerization where a bis-catechol such as, e.g., A1 (5,5',6,6'-tetrahydroxy-3,3,3',3'-tetramethyl-1,1'-spirobisindane) is allowed to react with a fluorinated arene such as, e.g., B1 (tetrafluoroterephthalonitrile) under basic conditions. Due to the rigidity and contorted nature of the backbone of the resulting polymers, these polymers are unable to pack tightly in the solid state and thus have at least 10 percent free volume and are intrinsically microporous.

PIMs may be blended with other materials. For example, a PIM may be blended with a material that itself is not an absorptive dielectric material. Even though not contributing to an analyte vapor response, such a material may be useful for other reasons. For example, such a material may allow the formation of a PIM-containing layer which has superior mechanical properties and the like. In one embodiment, PIMs may be dissolved in a common solvent with the other material to form a homogeneous solution, which may be cast to form an absorptive dielectric blend layer comprising both the PIM and the other polymer(s). PIMs may also be blended with a material that is an absorptive dielectric material (for example, zeolites, activated carbon, silica gel, hyper-cross-linked polymer networks and the like). Such materials may comprise insoluble materials that are suspended in a solution comprising of a PIMs material. Coating and drying of such a solution/suspension may provide a composite absorptive dielectric layer comprising both the PIM material and the additional absorptive dielectric material.

PIMs are typically soluble in organic solvents such as, for example, tetrahydrofuran, and can thus be cast as films from solution (e.g., by spin-coating, dip coating, or bar coating). However, characteristics (accessible thicknesses, optical clarity, and/or appearance) of films made from solutions of these polymers may vary markedly depending on the solvent or solvent system used to cast the film. For example, intrinsically microporous polymers of higher molecular weights may need to be cast from relatively unusual solvents (e.g., cyclohexene oxide, chlorobenzene, or tetrahydropyran) to generate films with desirable properties for use in vapor sensors as described herein. In addition to solution coating methods, the detection layer may be applied to the conductive base electrode by any other suitable method.

After a PIM is deposited (e.g., coated) or otherwise formed so as to comprise an absorptive dielectric layer, the material may be crosslinked using a suitable crosslinking agent such as, for example, bis(benzonitrile)palladium(II) dichloride. This process may render the absorptive dielectric layer insoluble in organic solvents, and/or may enhance certain physical properties such as durability, abrasion resistance, etc., which may be desirable in certain applications.

PIMs may be hydrophobic so that they will not absorb liquid water to an extent that the material swells significantly or otherwise exhibits a significant change in a physical property. Such hydrophobic properties are useful in providing an organic analyte vapor sensor element that is relatively insensitive to the presence of water. The material may however comprise relatively polar moieties for specific purposes.

Alternatively, in embodiments wherein the capacitive sensor element is used to detect humidity, the detection layer is preferably hydrophilic. For example, the detection layer may comprise a copolymer having monomeric units comprising

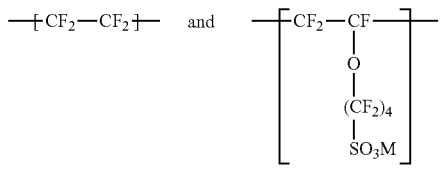

wherein M represents H (i.e., hydrogen) or an alkali metal (e.g., lithium, sodium, or potassium).

Such copolymers are described, for example, in U.S. Pat. No. 7,348,088 (Hamrock et al.). In one embodiment, the copolymer may be a random copolymer having a segment represented by the stoichiometric formula

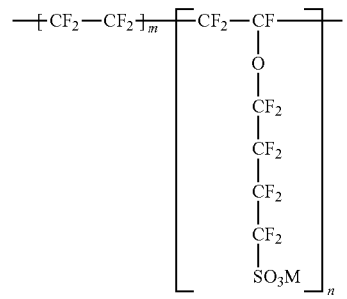

wherein m and n are positive integers (i.e., 1, 2, 3, etc.), and M is as previously defined. Other pendant groups such as, for example, perfluoroalkyl groups or perfluoroalkoxyl groups may also be present. Typically, substantially no (e.g., less than 5 mole percent of) other pendant groups are present in the copolymer; and more typically, no other pendant groups are present.

The copolymer may be made by the copolymerization of tetrafluoroethylene with 4'-fluorosulfonyl-1',1',2',2',3',3',4', 4'-octafluorobutyloxy-1,2,2-trifluoroethylene (i.e., $CF_2=CFO(CF_2)_4SO_2F$) followed by basic hydrolysis of the sulfonyl fluoride to the alkali metal sulfonate form or the sulfonic acid form. Additional co-monomers may be included to provide perfluoroalkyl or perfluoroalkyl ether pendant groups in the copolymer. Vinylidene fluoride may also be used as a monomer. Polymerization can be accomplished by any suitable method, including aqueous emulsion polymerization. The copolymer typically may have a sulfonate equivalent weight (i.e., the weight of the copolymer having one —$SO_3M$ group) of at least 500 grams per sulfonate equivalent, more typically at least 650 grams per sulfonate equivalent, and more typically at least 750 grams per sulfonate equivalent. The copolymer typically has a sulfonate equivalent weight of less than 1200 grams per sulfonate equivalent, more typically less than 1100 grams per sulfonate equivalent, or even less than or equal to 1000 grams per sulfonate equivalent. In some embodiments, the copolymer has a sulfonate equivalent weight in a range of from 500 to 1000 grams per sulfonate equivalent.

Examples of commercially available copolymers include those available under the trade designation 3M PERFLUOROSULFONIC ACID IONOMER from 3M Company, Saint Paul, Minn.

The detection layer may be deposited (for example, on the conductive electrode) by any suitable technique. Casting out of solvent or water, followed by heating to dry and optionally anneal the detection layer is typically an effective method. If desired, a fluorosulfonylated copolymer precursor may be cast out of solvent followed by hydrolysis, as discussed above.

Further details concerning an absorptive capacitance sensor element wherein the dielectric microporous material is an organosilicate material is described in U.S. Patent Appl. Publ. 2011/0254568 A1 (Thomas et al.).

The detection layer may have any thickness, but typically is in a range of from about 100 nanometers (nm) to 1 millimeter. More typically, the detection layer has a thickness in a range of from 500 to 10000 nm, or even from 700 to 3500 nm.

Further details concerning fabrication of capacitance sensor elements including PIMs, and principles of their operation, can be found in, for example, U.S. Patent Appl. Publ. Nos. 2011/0045601 A1 (Gryska et al.) and 2011/0031983 A1

(David et al.), and U.S. Provisional Appln. No. 61/388,146 entitled "Sensor Element, Method of Making the Same, and Sensor Device Including the Same" (Palazzotto et al.), filed Sep. 30, 2010.

Further details concerning fabrication of capacitance sensor elements including sulfonated fluoropolymers, and principles of their operation, can be found in, for example, in U.S. Provisional Appln. No. 61/494,578 entitled "Humidity Sensor and Sensor Element Therefor", filed Jun. 8, 2011 (Gryska et al.) and in U.S. Provisional Appln. No. 61/652,496, entitled "Humidity Sensor and Sensor Element Therefor", filed May 29, 2012 (Gryska et al.).

The detection layer may contain one or more additional components such as, for example, colorants, residual organic solvent, fillers, and/or plasticizers.

In one embodiment, the dielectric microporous material comprises a continuous matrix. Such a matrix is defined as an assembly (e.g., a coating, layer, etc.) in which the solid portion of the material is continuously interconnected (irrespective of the presence of porosity as described above, or of the presence of optional additives as discussed below). That is, a continuous matrix is distinguishable from an assembly that comprises an aggregation of particles (e.g., zeolites, activated carbons, or carbon nanotubes). For example, a layer or coating deposited from a solution will typically comprise a continuous matrix (even if the coating itself is applied in a patterned manner and/or comprises particulate additives). A collection of particles deposited via powder spraying, coating and drying of a dispersion (e.g., a latex), or by coating and drying of a sol-gel mixture, may not comprise a continuous network. However, if such a latex, sol-gel, etc., layer can be consolidated such that individual particles are no longer discernible, nor is it possible to discern areas of the assembly that were obtained from different particles, such a layer may then be considered to be a continuous matrix.

Figure 5:
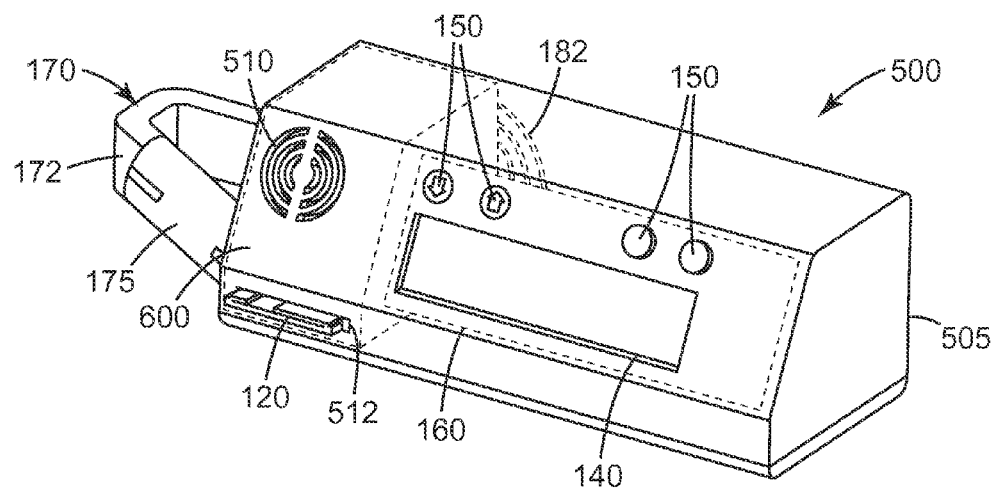
FIG. 5 is a perspective view of exemplary portable device 500 according to one embodiment of the present disclosure.

In another exemplary embodiment, shown in FIG. 5, portable device 500 comprises outer housing 505. Outer housing 505 includes inlet port 510 and outer slot 512 adapter to receive vapor sensor card 120. Attachment member 170, which includes handle 172 and spring clip 175, is affixed to outer housing 505 and provides convenient attachment to clothing and/or accessories worn by a user.

Sensor holder 600 is disposed within outer housing 505 and in electrical communication with operating circuit 160 through conductive members 182. Electronic display 140 is communicatively coupled to operating circuit 160 disposed within outer housing 505. Manually operable controls 150 allow a user to control the operating circuit and the electronic display.

Figure 6B:
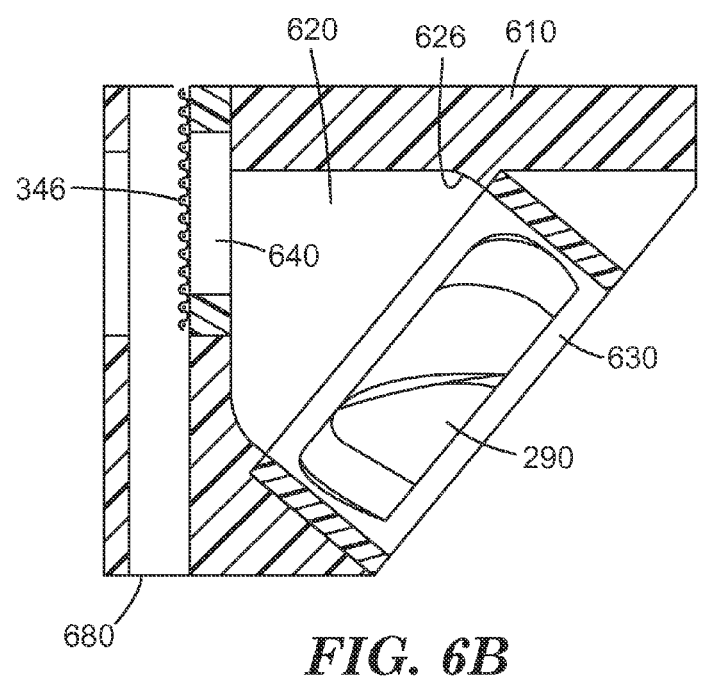
FIG. 6B is a cross-sectional view of inner housing 610 in FIG. 6A.
Figure 6A:
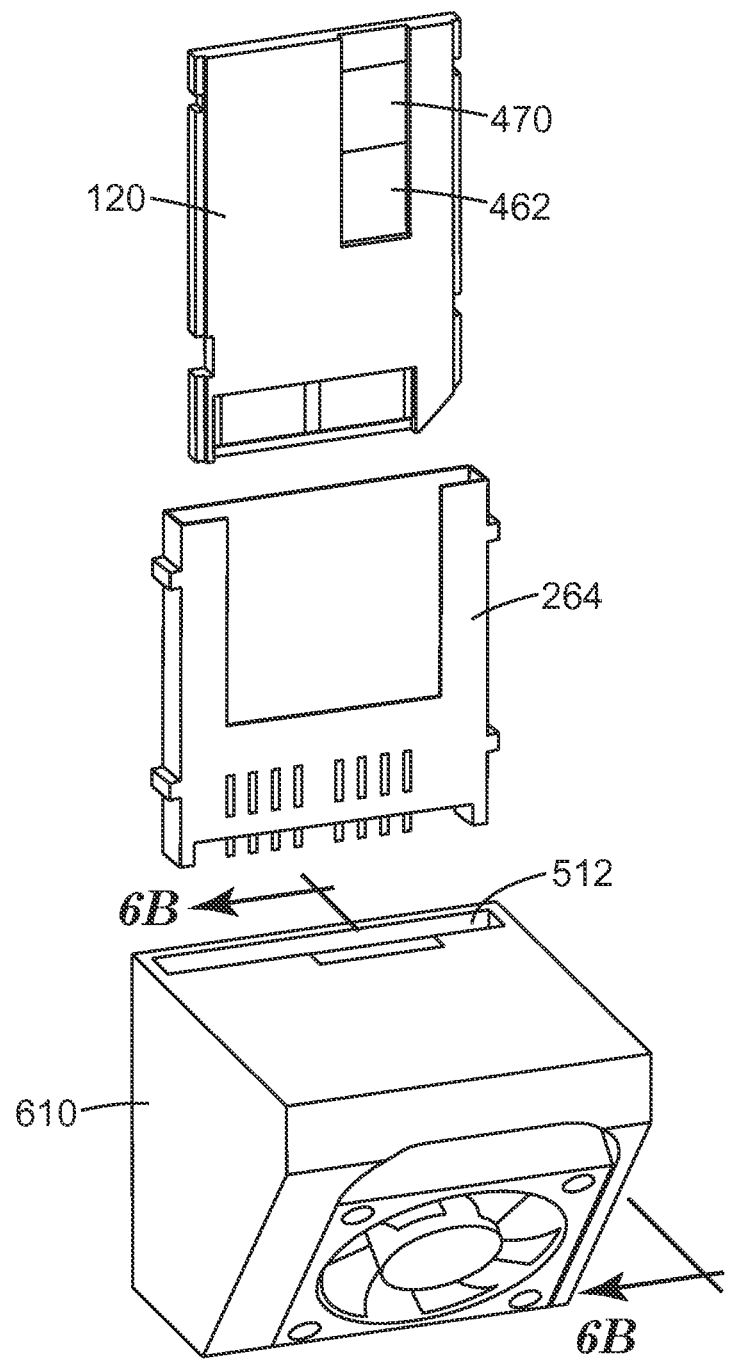
FIG. 6A is an exploded perspective view of inner housing 610 with vapor sensor card 120 and sensor card socket 264 inserted therein.
Figure 6C:
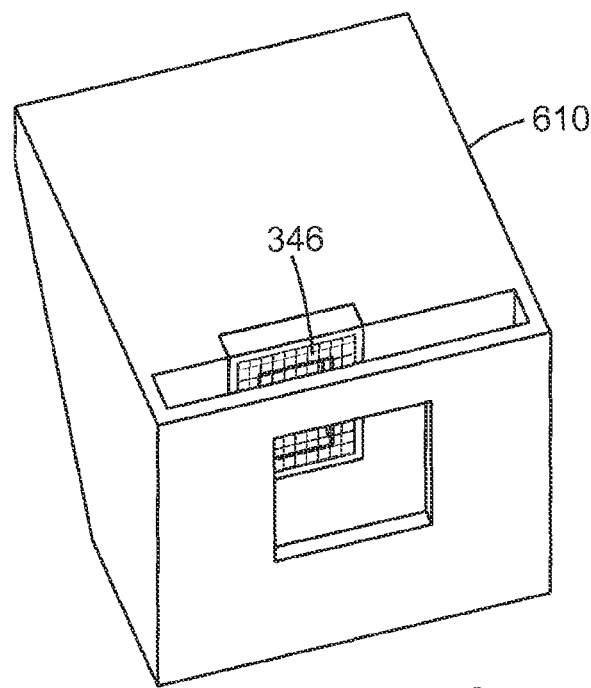
FIG. 6C is a perspective back view of inner housing 610 engaged with turbulent-flow-inducing member 346.

Referring now to FIGS. 6A and 6B, sensor holder 600 comprises inner housing 610, which includes gas intake chamber 620 (see FIG. 6B) in downstream fluid communication with inlet port 510. Gas intake chamber 620 comprises gas inlet 630 and gas outlet 640. Inner slot 680 retains a sensor card socket 264 adapted to engage vapor sensor card 120.

Figure 6D:
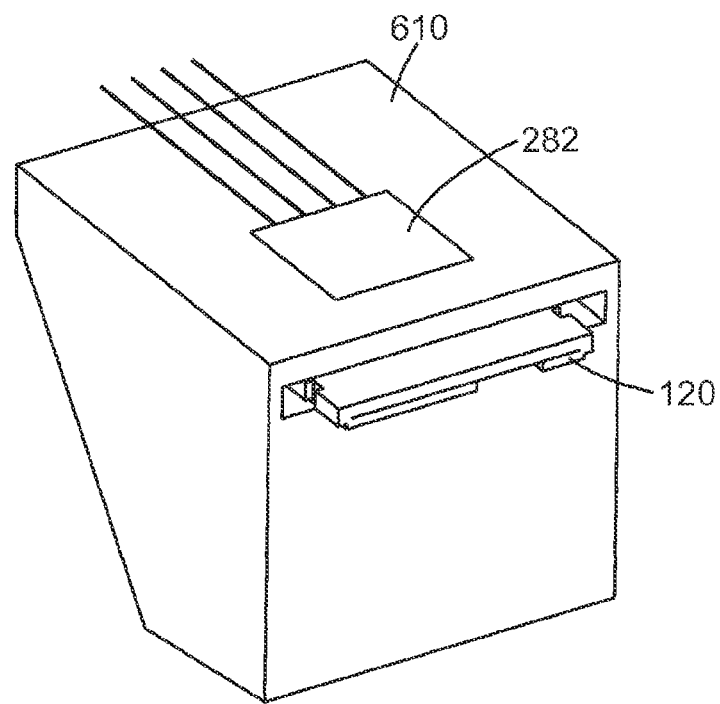
FIG. 6D is a perspective view of sensor holder 610 with vapor sensor card 120 inserted therein.

Referring now to FIG. 6D, electrical heater element 282, which contacts sensor card socket 264, is in electrical communication with operating circuit 160 and in thermal communication with sensor card socket 264.

Referring again to FIGS. 6A and 6B, fan 290, disposed within gas inlet 630, directs gas from inlet port 510 to inner slot 680. Turbulent-flow-inducing member 346 is adjacent to and extends across gas outlet 640.

Referring now to FIG. 6B, inner surfaces 626 of gas intake chamber 620 that are impinged upon by gas during use are rounded at intersections of adjacent walls to mitigate the problem of uneven gas flow (e.g., "dead" spots). While it may be convenient for a manufacturing standpoint to assemble inner housing 610 from multiple component members, it is also possible to fabricate it as a unitary piece (e.g., by molding or rapid prototyping). In this configuration, the outer housing acts as a mixing gas intake chamber where flow exiting the fan is allowed to redistribute prior to passing over the sensor element.

Select Embodiments of the Present Disclosure

In a first embodiment, the present disclosure provides a portable device comprising:
an outer housing including an inlet port and a outer slot adapted to receive a vapor sensor card;
an operating circuit disposed at least partially within the outer housing;
a sensor holder at least partially disposed within the outer housing, wherein the sensor holder comprises:
an inner housing including:
a gas intake chamber in downstream fluid communication with the inlet port, wherein the gas intake chamber has a gas inlet and a gas outlet;
a inner slot retaining a sensor card socket adapted to engage the vapor sensor card, wherein the inner slot is in fluid communication with the gas inlet through the gas intake chamber;
an electrical heater element in electrical communication with the operating circuit and in thermal communication with the sensor card socket;
a fan disposed such that it a directs gas from the inlet port to the gas outlet; and
a turbulent-flow-inducing member adjacent to and extending across at least a portion of the gas outlet.

In a second embodiment, the present disclosure provides a portable device according to the first embodiment, wherein the sensor card socket engages a vapor sensor card comprising:
a sensor housing having first and second opposed major surfaces; and
a capacitive sensor element partially disposed within the sensor housing, wherein taken together the capacitive sensor element and the sensor housing define a longitudinal channel along the first major surface of the housing wherein the capacitive sensor element comprises:
a conductive base electrode disposed on a support member;
a conductive porous electrode, wherein the conductive porous electrode comprises a portion of a bottom surface of the longitudinal channel, and wherein the conductive porous electrode comprises at least a portion of an outer surface of the vapor sensor card; and
a dielectric detection layer comprising a sorbent material disposed between the conductive base electrode and the conductive porous electrode; and
a first conductive pathway in electrical communication with the conductive base electrode and extending outside the sensor housing; and
a second conductive pathway in electrical communication with the conductive base electrode and extending outside the sensor housing,
wherein the capacative sensor element is in downstream fluid communication with the gas inlet.

In a third embodiment, the present disclosure provides a portable device according to the second embodiment, wherein the conductive base electrode and the conductive porous electrode comprise metal layers.

In a fourth embodiment, the present disclosure provides a portable device according to the second or third embodiment, wherein the conductive porous electrode comprises a porous gold electrode.

In a fifth embodiment, the present disclosure provides a portable device according to any one of the second to fourth embodiments, wherein the sorbent material comprises a sulfonated fluoropolymer.

In a sixth embodiment, the present disclosure provides a portable device according to any one of the second to fourth embodiments, wherein the sorbent material comprises a polymer of intrinsic microporosity containing dibenzodioxane linkages between monomeric units that are rigid, contorted, or rigid and contorted.

In a seventh embodiment, the present disclosure provides a portable device according to any one of the first to sixth embodiments, further comprising an electronic display communicatively coupled to the operating circuit.

In an eighth embodiment, the present disclosure provides a portable device according to any one of the first to seventh embodiments, further comprising at least one manually operable control for controlling the operating circuit.

In a ninth embodiment, the present disclosure provides a portable device according to any one of the first to eighth embodiments, wherein the fan is disposed at least partially within the gas inlet.

In a tenth embodiment, the present disclosure provides a portable device according to any one of the first to ninth embodiments, further comprising an attachment member affixed to the outer housing.

In an eleventh embodiment, the present disclosure provides a portable device according to any one of the first to tenth embodiments, wherein the inner housing comprises:
a first inner housing member including the gas inlet, and
a second inner housing member including the gas outlet, wherein the second inner housing member engages the first member to form the gas intake chamber.

In a twelfth embodiment, the present disclosure provides a vapor sensor card comprising:
a sensor housing having first and second opposed major surfaces, wherein the capacitive sensor element has a longitudinal channel abutting the first major surface, wherein the longitudinal channel has a bottom surface; and
a capacitive sensor element forming at least a portion of the bottom surface, wherein the capacitive sensor element comprises:
a conductive base electrode disposed on a support member;
a conductive porous electrode, wherein the conductive porous electrode comprises a portion of a bottom surface of the longitudinal channel, and wherein the conductive porous electrode comprises at least a portion of an outer surface of the vapor sensor card; and
a dielectric detection layer comprising a sorbent material disposed between the conductive base electrode and the conductive porous electrode; and
a first conductive pathway in electrical communication with the conductive base electrode and extending outside the sensor housing; and
a second conductive pathway in electrical communication with the conductive base electrode and extending outside the sensor housing.

In a thirteenth embodiment, the present disclosure provides a vapor sensor card according to the twelfth embodiment, wherein the sensor housing comprises upper and lower housing members.

Other modifications and variations to the present disclosure may be practiced by those of ordinary skill in the art, without departing from the spirit and scope of the present disclosure, which is more particularly set forth in the appended claims. It is understood that aspects of the various embodiments may be interchanged in whole or part or combined with other aspects of the various embodiments. All cited references, patents, or patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:
1. A portable device comprising:
an outer housing including an inlet port and an outer slot adapted to receive a vapor sensor card;
an operating circuit disposed at least partially within the outer housing;
a sensor holder at least partially disposed within the outer housing, wherein the sensor holder comprises:
an inner housing including:
a gas intake chamber in downstream fluid communication with the inlet port, wherein the gas intake chamber has a gas inlet and a gas outlet;
an inner slot retaining a sensor card socket adapted to engage the vapor sensor card, wherein the inner slot is in fluid communication with the gas inlet through the gas intake chamber, and wherein the sensor card socket engages a vapor sensor card, the vapor sensor card comprising:
a sensor housing having upper and lower housing members, the upper housing member defining a longitudinal through-opening; and
a capacitive sensor element received within the sensor housing, sandwiched between the upper and lower housing members, wherein the capacitive sensor element comprises:
a conductive base electrode disposed on a support member;
a conductive porous electrode, wherein the conductive porous electrode comprises a surface portion exposed outside through the longitudinal through-opening of the upper housing member to form a longitudinal channel, the longitudinal channel extending through the outer slot of the outer housing to provide an outlet for gas, and wherein the surface portion of the conductive porous electrode forms at least a portion of an outer surface of the vapor sensor card; and
a dielectric detection layer comprising a sorbent material disposed between the conductive base electrode and the conductive porous electrode; and a first conductive pathway in electrical communication with the conductive base electrode and extending outside the sensor housing; and a second conductive pathway in electrical communication with the conductive porous electrode and extending outside the sensor housing, wherein the capacitive sensor element is in downstream fluid communication with the gas inlet.

2. The portable device of claim 1, wherein the conductive base electrode and the conductive porous electrode comprise metal layers.

3. The portable device of claim 1, wherein the conductive porous electrode comprises a porous gold electrode.

4. The portable device of claim 1, wherein the sorbent material comprises a sulfonated fluoropolymer.

5. The portable device of claim 1, wherein the sorbent material comprises a polymer of intrinsic microporosity containing dibenzodioxane linkages between monomeric units that are rigid, contorted, or rigid and contorted.

6. The portable device of claim 1, further comprising an electronic display communicatively coupled to the operating circuit.

7. The portable device of claim 1, further comprising at least one manually operable control for controlling the operating circuit.

8. The portable device of claim 1 further comprising:
an electrical heater element in electrical communication with the operating circuit and in thermal communication with the sensor card socket;
a fan disposed such that it a directs gas from the inlet port to the gas outlet; and
a turbulent-flow-inducing member adjacent to and extending across at least a portion of the gas outlet.

9. The portable device of claims 1, further comprising an attachment member affixed to the outer housing.

10. The portable device of claim 1, wherein the inner housing comprises:

a first inner housing member including the gas inlet, and a second inner housing member including the gas outlet, wherein the second inner housing member engages the first member to form the gas intake chamber.

11. The portable device of claim 8, wherein the fan is disposed at least partially within the gas inlet.

12. A vapor sensor card comprising:
a sensor housing having upper and lower housing members, the upper housing member including a longitudinal through-opening; and
a capacitive sensor element sandwiched between the upper and lower housing members, wherein the capacitive sensor element has an upper surface portion exposed outside through the longitudinal through-opening of the upper housing member to form a longitudinal channel, and wherein the capacitive sensor element comprises:
a conductive base electrode disposed on a support member;
a conductive porous electrode, wherein the conductive porous electrode comprises the upper surface portion as a bottom surface of the longitudinal channel such that the upper surface portion of the conductive porous electrode forms at least a portion of an outer surface of the vapor sensor card; and
a dielectric detection layer comprising a sorbent material disposed between the conductive base electrode and the conductive porous electrode; and
a first conductive pathway in electrical communication with the conductive base electrode and extending outside the sensor housing; and
a second conductive pathway in electrical communication with the conductive porous electrode and extending outside the sensor housing.

\* \* \* \* \*